United States Patent [19]

Shields

[11] 4,247,404

[45] Jan. 27, 1981

[54] GLYOXAL-POLYAMINE-POLYBUTENYL SUCCINIC ANHYDRIDE REACTION PRODUCTS, PROCESS FOR THEIR PREPARATION AND LUBRICANTS AND FUELS CONTAINING SAME

[75] Inventor: Theodore C. Shields, Ashland, Ky.

[73] Assignee: Ashland Oil, Inc., Ashland, Ky.

[21] Appl. No.: 2,171

[22] Filed: Jan. 9, 1979

[51] Int. Cl.³ .................. C07D 207/12; C10L 1/22; C10M 1/20; C10M 1/32

[52] U.S. Cl. .................. 252/51.5 A; 44/63; 44/71; 260/326.26

[58] Field of Search ............. 252/51.5 A; 44/63, 71; 260/326.26

[56] References Cited

U.S. PATENT DOCUMENTS

| | | | |
|---|---|---|---|
| 3,369,021 | 2/1968 | Le Suer | 252/51.5 A |
| 3,458,530 | 7/1969 | Siegel et al. | 252/51.5 A |
| 3,647,691 | 3/1972 | Vineyard | 252/51.5 A |

*Primary Examiner*—W. J. Shine
*Attorney, Agent, or Firm*—Van D. Harrison, Jr.

[57] ABSTRACT

Diones and alkylamino derivatives of ethylene diamine and higher homolog polyamines are reacted to form an intermediate reaction product. This product subsequently is reacted with alkyl or alkenyl succinic anhydride to produce a dispersant for use in lubricants.

23 Claims, No Drawings

GLYOXAL-POLYAMINE-POLYBUTENYL SUCCINIC ANHYDRIDE REACTION PRODUCTS, PROCESS FOR THEIR PREPARATION AND LUBRICANTS AND FUELS CONTAINING SAME

NATURE OF THE INVENTION

This invention relates to novel oil-soluble dispersant compositions, a process for their preparation; and lubricants and fuels containing these compositions. More particularly, the invention is concerned with novel oil-soluble dispersant compositions produced by first reacting diones with ethylene and higher homolog polyamines to produce a first reaction product and subsequently reacting this product with alkyl or alkenyl succinic anhydride.

One of the principal problems associated with present day crankcase lubricants is that posed by the inevitable presence in the lubricant of foreign particles such as dirt, soot, water and decomposition products resulting from breakdown of the lubricating oil. Even if there were none of this latter contaminant present the very nature of the design of the modern internal combustion engine is such that a significant amount of sludge will accumulate in the crankcase. The accumulation of sludge presents a serious problem with respect to the efficient operation of the engine and it is desirable to prevent such deposition of sludge-like material. The problem of sludge formation has been with the automotive industry for many years and its solution has been approached by the use of known dispersants such as metal phenates and sulfonates but with only limited success.

It is accordingly a principal object of this invention to provide novel compositions of matter.

It is also an object of this invention to provide compositions which are adapted for use as additives in hydrocarbon oils.

It is also an object of this invention to provide compositions which are effective as dispersants in lubricating compositions.

It is another object of this invention to provide a novel process for the preparation of products which are effective as dispersants in lubricant compositions.

It is another object of this invention to provide improved hydrocarbon oil compositions.

It is another object of this invention to provide improved lubricating compositions.

It is another object of this invention to provide improved fuel compositions.

SUMMARY OF THE INVENTION

Briefly stated, this invention comprises in one aspect a process for preparing a dispersant for use in lubricants and fuels comprising:

1. Reacting an alkylamino substituted ethylene diamine or homologous polyamine of the general formula:
H[(HN(CH$_2$)$_3$]$_m$NHCH$_2$CH$_2$NH[(CH$_2$)$_3$NH]$_n$
where m+n is between 2 and 6 with a dione or mixture of diones of the structural formula:

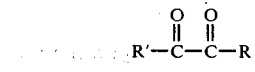

where R and R' are each either hydrogen or an alkyl radical of 2 to 4 carbon atoms; and 2. Reacting the resulting intermediate reaction product with polybutenyl succinic anhydride.

The resultant product is an effective dispersant in lubricating oil compositions.

In another aspect, this invention comprises the reaction product obtained by the above described process. In still another aspect, this invention comprises a major amount of lubricant and a minor amount of the reaction product described above. In still another aspect, this invention comprises a method for treating a lubricant or fuel by combining therewith effective amounts of the afore-described dispersant composition.

DETAILED DESCRIPTION OF THE INVENTION

The dione used in the making of the dispersant of this invention is one having the structural formula:

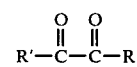

where R is either hydrogen or an alkyl radical of 2 to 4 carbon atoms and R' is either hydrogen or an alkyl radical of 2 to 4 carbon atoms. Preferably R' and R are hydrogen so that the most preferable dione is glyoxal which has the structural formula:

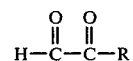

In water solution glyoxal is believed to be a mixture of a series of hydrated forms. Commercially, glyoxal is supplied as a light-yellow aqueous solution containing a minimum of 30% by weight of glyoxal, and small amounts of ethylene glycol, glycolic acid, formic acid, and formaldehyde.

Other diones which can be used include pyruvic aldehyde (CH$_3$COCHO) and 2,3-butanedione.

Preferred alkylamino derivatives of ethylene diamine are:

(a) 4,7-diazadecane-1,10-diamine
(b) 4,7,11-triazatetradecane-1,14-diamine
(c) 4,8,11,15-tetraazaoctadecane-1,18-diamine
(d) a mixture of 60% to 40% of 4,7,11-triazatetradecane-1,14-diamine and 40% to 60% 4,8,11,15-tetraazaoctadecane-1,18-diamine.
(e) other mixtures of the above named diamines; and
(f) mixtures of one or more of the above named amines also containing up to 50% by weight of 3-azahexane-1,6-diamine.

Of these amines the 4,7-diazadecane-1,10-diamine and a mixture of 60% of 4,7,11-triazatetradecane-1,14-diamine and 40% 4,8,11,15-tetraazaoctadecane-1,18-diamine are most preferred.

The alkenyl succinic anhydride used is that readily prepared by reacting maleic anhydride with an organic compound having a double bond at its end to thereby give compounds of the general formula:

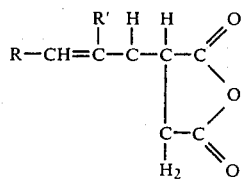

wherein R and R' can be hydrogen or hydrocarbon radicals including aliphatic, acyclic, aromatic, etc., although at least one of said R and R' must be an aliphatic hydrocarbon group. The total number of carbon atoms in R and R' will generally be 40 to 250 and preferably 70 to 120. Because of its ready availability and low cost, the alkenyl portion of the molecule is preferably obtained by reacting a polymer of a $C_2$ to $C_5$ monoolefin with maleic anhydride, said polymer generally having a molecular weight of about 500 to 1600 and preferably about 800 to 1300 and more preferably about 650 to 1400. A preferred example of such olefinic polymer is polybutene. The preparation of alkenyl succinic anhydrides is by now well-known in the art. The aliphatic substitution on the succinic anhydride can also be a saturated alkyl group of the same carbon atom number.

Throughout the remainder of the specification glyoxal will be specified as the dione used. It is not to be inferred however, that the other diones previously mentioned could not also be used.

As the first step in the preparation of the composition of this invention, the glyoxal and the polyamine are mixed together preferably in a mole ratio of 1 mole of glyoxal to 2 moles of polyamine. An excess of either reactant can be used but is not particularly desirable.

If desired, this first reaction step can be conducted in the presence of substantially inert organic liquid diluents. The presence of the diluent can facilitate temperature control and the mixing of the reactants. If a diluent is selected which will form an azeotrope with water, the diluent assists in the removal of water. Suitable diluents include, for example, the normally aliphatic, cycloaliphatic, and aromatic hydrocarbons and the corresponding halogenated hydrocarbons, particularly chlorinated hydrocarbons, such as benzene, toluene, xylene, chlorobenzene, hexane, heptane, cyclohexane, mineral oil, mixtures thereof, and the like. Water may also be used as the inert liquid diluent in the step. However, for commercial practicability it is preferred to add only a minimum amount of water.

The reaction between the glyoxal and the amine is exothermic and the temperature is maintained between $-30°$ C. and $120°$ C. or preferably between $0°$ C. and $60°$ C. until the evolution of heat subsides. The mixture is then refluxed for a period of time sufficient to insure reaction preferably at a temperature of around $50°$ C., and is then subjected to stripping preferably at a reduced pressure and a maximum temperature of $200°$ C. to remove water of reaction and/or carrier liquid. The resulting product is the desired intermediate product.

The polyalkenyl succinic anhydride can be reacted with the intermediate product as it is upon completion of the first reaction or after it is subjected to desired purification techniques. For example, the intermediate reaction product may be filtered before contacting it with the polyalkenyl succinic anhydride. The reaction product may be stripped at reduced pressure to remove substantially all water and other volatiles present. Blowing the reaction product with dry inert gases such as nitrogen, helium and the like also assist in removing water. However, it is not necessary that any of these purification techniques be applied to the first reaction mixture before it is reacted with the alkenyl succinic anhydride. The application of any of the desired purification techniques may be postponed until after completion of the reaction of the intermediate reaction product with the alkenyl succinic anhydride.

The intermediate reaction product from the first reaction step and the alkenyl succinic anhydride are generally reacted at temperatures ranging from about $25°$ C. up to the decomposition point. Generally, however, the intermediate reaction product and the alkenyl succinic anhydride will be reacted at temperatures in the range of about $25°$ C. up to about $300°$ C. and preferably at temperatures of about $100°$ C. up to about $200°$ C. The time for contacting the intermediate reactive product with the alkenyl succinic anhydride will vary with the amount of materials employed, the specific reactants involved, the temperature and the like. However, good results can be obtained by contacting the intermediate reaction product with the alkenyl succinic anhydride for a period of time varying from about 0.1 to 10.0 hours. Optimum duration of contact for a given combination and temperature can be easily ascertained within this range. The intermediate reaction product is reacted with the polyalkenyl succinic anhydride in a mole ratio of between 6.0 and 1.5 moles of succinic anhydride to 2 moles of the initial polyamine used to make the intermediate reaction product and preferably in a ratio of between 4.5 and 3.0 moles of succinic anhydride to 2 moles of initial polyamine.

This second reaction between intermediate reaction product and succinic anhydride can also be conducted, if desired, in the presence of substantially inert organic liquid diluents. If a diluent is selected which will form an azeotrope with water the diluent assists in the removal of water. Suitable diluents include, for example, the normally aliphatic, cycloaliphatic, and aromatic hydrocarbons and the corresponding halogenated hydrocarbons, particularly chlorinated hydrocarbons, such as benzene, toluene, xylene, chlorobenzene, hexane, heptane, cyclohexane, mineral oil, mixtures thereof, and the like.

The product resulting from this second reaction between the alkenyl succinic anhydride and intermediate reaction product is the desired dispersant. It is subjected to desired purification techniques. For example, it may be filtered and/or it may be stripped at reduced pressure to remove substantially all water and other volatiles present. Blowing the reaction mixture with dry inert gases such as nitrogen, helium, and the like also assist in removing water. The oil-soluble compositions of the present invention is the resulting mixture of oil-soluble materials. The specific nature of these compositions of this invention are best described in terms of their process of preparation.

Generally, the oil-soluble compositions of this invention can be used in fuels and lubricants alone or in combination with other conventional additives. When employed as sludge-dispersing additives for lubricants the oil-soluble compositions can be used in amounts such that they comprise from about 0.01% to about 30% by weight of the lubricant depending on the use to which the lubricant is to be put and the presence or absence of other additives, especially dispersants or detergents. Ordinarily, they will comprise at least about 0.1% and up to about 10% by weight of the lubricant although, under unusually harsh operating conditions such as are encountered in certain diesel engines, amounts of 10% to 30% are beneficially employed, particularly in the absence of other detergent or dispersant additive.

The oil-soluble compositions of this invention can be effectively employed in a variety of lubricating compositions based on diverse oils of lubricating viscosity such as a natural or synthetic lubricating oil, or suitable mixtures thereof. The lubricating compositions contemplated include principally crankcase lubricating oils for spark-ignited and compression-ignited internal combustion engines including automobile and truck engines, two-cycle engine lubricants, aviation piston engines, marine and railroad diesel engines, and the like. However, automatic transmission fluids, transaxle lubricants, gear lubricants, metal-working lubricants, hydraulic fluids, and other lubricating oil and grease compositions can benefit from the incorporation of the present additives.

The oil-soluble compositions of this invention are normally used in conjunction with other conventional lubricating oil additives. The conventional additives include extreme pressure agents, metal containing detergents such as normal and basic oil-soluble alkaline earth metal phenates, petrosulfonates, and salicylates, viscosity index improving agents, oxidation inhibitors, anti-foam agents, ashless dispersants, corrosion inhibitors, and the like.

In fuels, the oil-soluble compositions of the invention promote engine cleanliness by reducing or eliminating harmful deposits in the fuel system, engine and exhaust system through their dispersant capabilities. They are primarily intended for use in the normally liquid petroleum distillate fuels, that is, the petroleum distillates which boil in the range characteristic of petroleum fuels such as gasolines, fuel oil, diesel fuels, aviation fuels, kerosene and the like. When employed in fuels, they are generally employed in lower concentrations than in lubricants, for example, in amounts of from about 0.0001% to about 2% by weight and generally in amounts of from about 0.001% to about 0.5% by weight. As in the case of lubricants, other conventional fuel additives can be present in the fuel compositions contemplated herein. These conventional additives include lead scavengers, deicers, anti-screen clogging agents, neutral or basic oil-soluble alkaline earth metal sulfonates, phosphonates, or carboxylates, other ashless dispersants, antifoulants, demulsifiers, and the like.

The following examples illustrate preferred embodiments of the process and the oil-soluble compositions of this invention.

EXAMPLES

Lube oil dispersants were prepared from the following amine materials:
A. 4,7-diazadecane-1,10-diamine
B. 60% 4,7,11-triazatetradecane-1,14-diamine and 40% 4,8,11,15-tetrazaoctadecane-1,18-diamine
C. 40% 4,7,11-triazatetradecane-1,14-diamine and 60% 4,8,11,15-tetrazaoctadecane-1,18-diamine using a 40% aqueous solution of glyoxal in the proportions as follows and added water:

| Run No. | 2-66 | 3-9 | 3-7 |
|---|---|---|---|
| Amine | A | B | C |
| Amine grams (moles) | 174(1.0) | 100.3(0.4) | 104.8(0.4) |
| Distilled Water ml. | 300 | 200 | 200 |
| 40% Glyoxal Solution grams (moles) | 72.5(0.5) | 29.0(0.2) | 29.0(0.2) |
| Product, grams | 185.1 | 104.6 | 113.2 |

In each run the amine was charged to a one-liter stirred flask. Distilled water 1.7 to 2.0 grams water per gram of amine) was added and the solution cooled to 0° C. The 40% glyoxal aqueous solution was then added with the reaction temperature maintained between 0° C. and 2° C. The mixture was heated to reflux (approximately 100° C.) over a 30 minute period. Water was distilled overhead at a 60° C. maximum temperature under a vacuum of 75-100 mm of mercury. Isopropanol was then added to aid in the removal of residual water and the solvents again removed under vacuum at a maximum temperature of 120° C. The resulting products were the desired intermediate material.

The dispersant composition was prepared by reacting each of the intermediate materials with polybutenyl succinic anhydride (PBSA) having an average molecular weight of approximately 1,000. The PBSA was charged to a flask, heated to 110°-120° C., and the intermediate product obtained from the initial reaction added. The reaction mass was stirred at 165°±5° C. for 1½ hours and the temperature was then raised to 210° C.±5° C. and maintained for 1 hour with frequent nitrogen stripping to remove water condensed in the flask. The resulting dispersant product was diluted with 150 neutral oil to give a 66.7% active material.

The proportions of reactants in the second step were as follows:

| Run No. | 2-66 | 3-9 | 3-7 |
|---|---|---|---|
| PBSA grams (moles) | 500(0.5) | 400(0.4) | 400(0.4) |
| Intermediate Reaction Product grams | 46.25(0.125) | 42.0(0.101) | 57.2(0.101) |
| Product grams | 536 | 443.5 | 449.5 |
| Sludge Ratio | 0.97 | 0.99 | 0.69 |

Sludge spot tests of each of the three dispersants obtained from the preceeding procedure were conducted as follows:

A blend of 0.25 grams of each of the dispersants, 2.0 grams 150 neutral oil, and 4.0 grams used sludge-containing oil, containing no other dispersant was prepared. The blend was stirred at 130° C. and samples were removed after 30 minutes, 1½ hours, 4 hours and 7 hours. Three drops each sample of the blend were placed on blotter paper and allowed to spread radially by adsorption over the paper. The spots were measured 24 hours after the start of the test. The ratio of the diameter of the dark spot to the diameter of the total spot was recorded as the sludge ratio. A ratio of 1 indicates a dispersance of 100% and represents complete dispersance.

The dispersant product resulting from Run No. 2-66 was tested in V-C engine tests. The procedure for this engine test is well known to those skilled in the art.

The weight percents of dispersant used and the types of lubricating oil used are shown in the table below. For comparison purposes a test was also made of a commercial dispersant. Results were as shown below:

| Run No. | Oil Type | Wt. % of Active Dispersant | Wt. % of Calcium Sulfonate | Average Sludge | Average Varnish | Piston Varnish |
|---|---|---|---|---|---|---|
| 65 | SAE10W40 | 2.7(1) | 2 | 8.93 | 6.98 | 7.62 |
| 70 | SAE10W40 | 2.7(1) | 1 | 9.28 | 7.82 | 8.02 |
| 60 | SAE 30 | 2.7(1) | 2 | 9.25 | 7.53 | 7.79 |
| 63 | SAE 30 | 4(1) | 2 | 9.55 | 8.22 | 8.23 |
| 51 | SAE 30 | 2.7(2) | 2 | 9.45 | 7.21 | 7.54 |
| 41 | Ford Ref.Oil | — | | 8.79 | 7.77 | 8.21 |
| 53 | | — | | 8.19 | 7.52 | 7.20 |
| Desired Minimum | | | | 8.70 | 8.00 | 7.90 |

(1)Dispersant prepared similarly to that in Run No. 2-66
(2)Commercial dispersant

I claim:

1. A process for preparing oil soluble compositions useful as dispersants in lubricating oil compositions comprising the steps of:

(a) reacting at a temperature of between about −30° C. and about 120° C. an alkylamino substituted ethylene diamine or a homolog thereof having the structural formula:

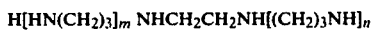

with a dione or mixture of diones of the structural formula:

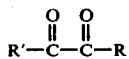

where m+n is between 2 and about 6 and R and R' are each either hydrogen or an alkyl radical of 1 to 4 carbon atoms thereby obtaining a first reaction product; and (b) reacting said first reaction product with a polyalkenyl succinic anhydride having a molecular weight between about 500 and about 1600 at a temperature between about 25° C. and about 200° C.

2. The process of claim 1 wherein the polyalkenyl succinic anhydride has a molecular weight of between about 650 and about 1400.

3. The process of claim 1 wherein said diamine is selected from the group consisting of 4,7-diazadecane-1,10-diamine, 4,7,11-triazatetradecane-1, 14-diamine, 4,8,11,15-tetraazaoctadecane-1,18-diamine, mixtures thereof, and mixtures thereof also containing up to about 50% by weight of 3-azahexane-1,6-diamine.

4. The process of claim 1 wherein said diamine is 4,7-diazadecane-1,10-diamine.

5. The process of claim 1 wherein said diamine is 4,7,11-triazatetradecane-1,14-diamine.

6. The process of claim 1 wherein said diamine is 4,8,11,15-tetraazaoctadecane-1,18-diamine.

7. The process of claim 1 wherein said diamine is a mixture of 60% to 40% of 4,7,11-triazatetradecane-1,14-diamine and 40% to 60% 4,8,11,15-tetraazaoctadecane-1,18-diamine.

8. The process of claim 1 wherein said diamine contains up to 50% by weight of 3-azahexane-1,6-diamine.

9. The process of claim 1 wherein said dione is glyoxal.

10. The process of claim 1 wherein said dione is pyruvic aldehyde.

11. The process of claim 1 wherein said dione is 2,3-butanedione.

12. The process of claim 1 wherein said polyamine is 4,7-diazadecane-1, 10 diamine and said dione is glyoxal.

13. The process of claim 1 wherein said diamine is a mixture of between about 40% and 60% by weight of 4,8,11,15-tetraaza-octadecane-1,18 diamine and 60% to 40% by weight of 4,7,11-triazatetradecane-1,14 diamine.

14. The process of claim 1 wherein the mole ratio of amine to dione is about 2 to 1.

15. The process of claim 1 wherein the mole ratio of polyalkenyl succinic anhydride to amine is between about 6.0 to 2 and about 1.5 to 2.

16. The process of claim 1 wherein the mole ratio of polyalkenyl succinic anhydride to amine is between about 4.5 to 2 and about 3.0 to 2.

17. The process of claim 1 wherein the reaction in step (a) is conducted at a temperature between about 0° C. and about 60° C. and the reaction of step (b) is conducted at a temperature of between about 25° C. and 300° C.

18. The product produced by the process of claim 1, 2, 3, 4, 5, 6, 7, 8, 9, 10, 11, 12, 13, 14, 15, 16 or 17.

19. A process for treating a hydrocarbon liquid comprising adding to said hydrocarbon liquid the product produced by the process of claim 1, 2, 3, 4, 5, 6, 7, 8, 9, 10, 11, 12, 13, 14, 15, 16 or 17.

20. The process of claim 19 wherein said hydrocarbon liquid is a lubricating oil.

21. The process of claim 19 wherein said hydrocarbon liquid is a fuel.

22. A lubricating oil composition containing a major proportion of lubricating oil and a minor proportion of the product produced by the process of claim 1, 2, 3, 4, 5, 6, 7, 8, 9, 10, 11, 12, 13, 14, 15, 16 or 17.

23. A hydrocarbon fuel composition containing a major proportion of hydrocarbon fuel and a minor portion of the product produced by the process of claim 1, 2, 3, 4, 5, 6, 7, 8, 9, 10, 11, 12, 13, 14, 15, 16 or 17.

* * * * *